United States Patent
Fuchs et al.

(10) Patent No.: US 11,628,380 B2
(45) Date of Patent: Apr. 18, 2023

(54) SYSTEMS AND METHODS FOR EXTRACTION OF BIOMASS MATERIALS

(71) Applicant: Prototype Garage, LLC, Little Canada, MN (US)

(72) Inventors: Greg Fuchs, River Falls, MN (US); Greg White, Hugo, MN (US); Jeremy Granquist, St. Paul, MN (US); Olaf Lee, Forest Lake, MN (US)

(73) Assignee: Prototype Garage, LLC, Little Canada, MN (US)

( * ) Notice: Subject to any disclaimer, the term of this patent is extended or adjusted under 35 U.S.C. 154(b) by 0 days.

(21) Appl. No.: 17/829,989

(22) Filed: Jun. 1, 2022

(65) Prior Publication Data

US 2022/0297028 A1     Sep. 22, 2022

Related U.S. Application Data

(62) Division of application No. 17/013,527, filed on Sep. 4, 2020, now Pat. No. 11,376,522.

(60) Provisional application No. 62/896,108, filed on Sep. 5, 2019.

(51) Int. Cl.
   *B01D 11/02*     (2006.01)
   *C07C 7/10*      (2006.01)

(52) U.S. Cl.
   CPC ...... *B01D 11/0288* (2013.01); *B01D 11/0203* (2013.01); *C07C 7/10* (2013.01)

(58) Field of Classification Search
   CPC .... B01D 11/0203; B01D 11/0288; C07C 7/10
   See application file for complete search history.

(56) References Cited

U.S. PATENT DOCUMENTS

| | | | | |
|---|---|---|---|---|
| 2013/0192592 A1* | 8/2013 | Mraz | ............ | C08B 37/0057 127/37 |
| 2014/0090728 A1* | 4/2014 | Kotsiopoulos | ...... | F04B 35/04 137/560 |
| 2015/0315502 A1* | 11/2015 | Foody | .......... | C07C 37/74 518/703 |

* cited by examiner

*Primary Examiner* — Bradley R Spies
(74) *Attorney, Agent, or Firm* — O'Connor & Company; Ryan P. O'Connor

(57) ABSTRACT

Some variations provide a system for extracting a product from biomass, comprising: a process chamber having an internal volume; one or more mechanical elements configured to controllably and reversibly mechanically seal the process chamber and reduce the internal volume to mechanically compress the biomass; a fluid port in flow communication with the process chamber; and a collection subsystem in flow communication with the fluid port. Other variations provide a method of extracting a product from biomass, the method comprising: introducing biomass into a process chamber; mechanically sealing the process chamber; mechanically compressing the biomass to release a first fluid material; mechanically decompressing the biomass; introducing an extraction solvent into the process chamber; maintaining process-chamber pressure from about 1 bar to about 1000 bar, wherein the extraction solvent extracts a second fluid material; and recovering the second fluid material from the process chamber. High processing throughput is enabled with this invention.

19 Claims, 5 Drawing Sheets

SYSTEMS AND METHODS FOR EXTRACTION OF BIOMASS MATERIALS

PRIORITY DATA

This patent application is a divisional application of U.S. patent application Ser. No. 17/013,527, filed on Sep. 4, 2020, which claims priority to U.S. Provisional Patent App. No. 62/896,108, filed on Sep. 5, 2019, each of which is hereby incorporated by reference herein.

FIELD OF THE INVENTION

The present invention generally relates to methods and systems for extracting botanical products from biomass materials, and products produced from these methods and systems.

BACKGROUND OF THE INVENTION

Botanical extracts and oils represent an important agricultural commodity. A botanical extract is an herbal ingredient with desirable flavor, aroma, or nutritive quality that is removed from the tissue of a plant, usually by treating it with a solvent. Botanical extracts have been used as a source of medicine throughout history and continue to serve as the basis for many pharmaceuticals, cosmeceuticals, and nutraceuticals today. Valuable botanical extracts include chamomile, dandelion, *echinacea*, marigold, lavender, hemp, and many other therapeutic plants and herbs.

Solvent extractions of botanical oils have occurred for centuries. Most early applications employed the use of commonly available oils like olive oil and vegetable oils, based on direct contact of the oil with the plant material or seeds of the desired oil. These were used in early medicine, food enhancements, and preservatives. This conventional process was very inefficient and only a minor portion of the plant's compounds were transferred to the oil carrier. Steam stripping was later used and proved to be more efficient. Steam extractions are widely used today. However, the high temperatures of the steam stripping cycle damage many targeted compounds.

One problem that exists in botanical extraction processing currently is that manufacturing methods are limited in throughput capacity. Present systems are generally small, single-batch, mixed-phase solvent systems designed and operated for small throughputs. For example, in some prior-art systems, an operator manually fills an extraction vessel, rinses the plant material, and then waits to remove excess solvent via evaporation, pressure, or spinning.

Industrial-scale processing of commodity products like soybeans and corn is performed by using solvent extraction, mechanical pressing, or each process sequentially. Many higher-value feedstocks, such as essential oils, bioactive compounds, and antioxidants require processing that avoids potentially harmful solvents and high heat. These processes include cold pressing and the use of solvents such as supercritical carbon dioxide. The advantages of these systems include less damage or chemical alteration of temperature-sensitive compounds in the extract and the use of solvents which are not biologically harmful and that are easy to separate from the extracted products. The disadvantage of these systems is typically low throughput, lower recovery rates, and high operating costs. These disadvantages limit the use of these processes to products with high market values or to markets which place a premium on safer processing methods.

Because the market for botanical extraction is rapidly expanding, there is an immediate need for higher-efficiency processing. There is a real need to overcome the aforementioned gaps in processes and equipment, particularly those using extraction solvents and/or low-temperature mechanical processing.

It is especially desired to overcome low throughput and recovery rates, and improve loading and unloading capabilities, over currently available equipment and processes. A solution to these problems would have widespread applicability in industrial processes.

SUMMARY OF THE INVENTION

The present invention addresses the aforementioned needs in the art, as will now be summarized and then further described in detail below.

Some variations of the invention provide a system configured for extracting one or more products from a biomass material, the system comprising:

a process chamber having an internal volume suitable for containing a biomass material and optionally an extraction solvent;

one or more mechanical elements configured to (i) controllably and reversibly mechanically seal the process chamber from the environment and (ii) controllably and reversibly reduce the internal volume to mechanically compress the biomass material within the process chamber;

a fluid port disposed in flow communication with the process chamber; and a collection sub-system disposed in flow communication with the fluid port, wherein the collection sub-system is configured to recover one or more products from the process chamber.

In some embodiments, at least one of the mechanical elements is a hydraulic piston. Preferably, a common mechanical element is configured both to controllably and reversibly mechanically seal the process chamber from the environment and controllably and reversibly reduce the internal volume to mechanically compress the biomass material within the process chamber. The process chamber may be a single-piston pressure chamber or a dual-piston pressure chamber, for example.

In some embodiments, at least one of the mechanical elements is configured to controllably compress the extraction solvent within the process chamber. In these or other embodiments, at least one of the mechanical elements is configured to controllably release the extraction solvent out of the process chamber through the fluid port.

The extraction solvent may be selected from the group consisting of carbon dioxide, alkanes, alkenes, alcohols, water, and combinations thereof, for example.

In some embodiments, the collection sub-system includes at least one collection chamber having a collection volume, wherein the collection sub-system includes an additional mechanical element configured to controllably and reversibly adjust the collection volume. Because the collection volume is adjustable, and when there is a good seal, the collection pressure contained within the collection chamber is adjustable to assist in recovery of one or more products.

Other variations of the present invention provide a method of extracting one or more products from a biomass material, the method comprising:

(a) introducing a starting biomass material into a process chamber;

(b) mechanically sealing the process chamber;

(c) mechanically compressing the starting biomass material to physically release at least a first fluid material, thereby generating a compressed biomass material;

(d) mechanically decompressing the compressed biomass material, thereby generating an intermediate biomass material;

(e) introducing an extraction solvent into the process chamber;

(f) maintaining process-chamber pressure from about 1 bar to about 1000 bar for an extraction time, wherein the extraction solvent extracts at least a second fluid material from the intermediate biomass material, thereby generating a left-over biomass material; and (g) recovering at least the second fluid material from the process chamber.

In some embodiments, the extraction solvent is pre-blended with the starting biomass material prior to step (b). Alternatively, or additionally, the extraction solvent may be introduced into the process chamber during step (b), step (c), and/or step (d), or between any of these steps, or after step (d).

In some embodiments, step (b) utilizes a hydraulic piston to mechanically seal the process chamber. The same hydraulic piston, or another hydraulic piston, may be utilized to mechanically compress the starting biomass material in step (c). Optionally, step (c) may be assisted by a solvent that dissolves or suspends the first fluid material; this solvent, when employed, may be the same or different than the extraction solvent. The hydraulic piston may be retracted prior to pumping extraction solvent into the process chamber, thereby increasing the volume of the process chamber while maintaining the seal so that the solvent is retained in the process chamber.

In step (f), the extraction solvent may be compressed using the same mechanical element as used in step (b), to reach the process-chamber pressure. In some embodiments, for example, a hydraulic piston is positioned to compress the extraction solvent to reach the process-chamber pressure.

In various embodiments, the extraction solvent is selected from the group consisting of carbon dioxide, alkanes, alkenes, alcohols, water, and combinations thereof. In some embodiments, the extraction solvent is liquid carbon dioxide, supercritical carbon dioxide, or a combination thereof. In some preferred embodiments, the extraction solvent is supercritical carbon dioxide.

In some embodiments, the process-chamber pressure is selected from about 50 bar to about 500 bar. The extraction time may be from about 0.1 minute to about 1 hour, for example. Step (f) may be carried out at an extraction temperature from about −50° C. to about 100° C., for example. In step (f), the ratio of the extraction solvent to the intermediate biomass material may be selected from about 1 to 20 on a mass basis, for example.

The method may further include recovering the first fluid material. The first fluid material and the second fluid material may be chemically the same or different.

In step (g), the second fluid material may be mechanically released from the process chamber. Typically, the extraction solvent is mechanically released along with the second fluid material, although the mechanical release may be sequential by varying pressure and/or temperature. In some embodiments, a hydraulic piston is used to mechanically release the second fluid material and the extraction solvent. In some embodiments, left-over biomass material is compressed by the hydraulic piston, which is convenient for recovery of the left-over biomass material.

Optionally, the method further comprises repeating steps (d), (e), and (f) a plurality of times. During cycling, the process-chamber pressure, the extraction time, and/or extraction temperature may be adjusted.

Some variations of the disclosure provide a collection system configured for recovering one or more products from an extracted biomass material, the collection system comprising:

at least one collection chamber having a collection volume;

an inlet to the collection chamber, configured to introduce a biomass-extraction liquid;

a mechanical element configured to controllably and reversibly adjust the collection volume, wherein collection pressure contained within the collection chamber is adjustable to assist in recovery of one or more products from the biomass-extraction liquid.

In some embodiments of the collection system, the mechanical element is a hydraulic piston.

In some embodiments of the collection system, the mechanical element is configured both to controllably and reversibly mechanically seal the collection chamber from the environment and controllably and reversibly reduce the chamber volume.

In some embodiments of the collection system, the mechanical element is configured to controllably release the biomass-extraction liquid out of the collection chamber.

The collection system may include multiple collection chambers each with a distinct collection volume, wherein for each collection chamber, there is a mechanical element configured to controllably and reversibly adjust the respective collection volume of that collection chamber.

Still other variations of the disclosure provide a pumping system configured for pumping a liquid into a process chamber, the pumping system comprising:

at least one process chamber having a process volume;

an inlet to the process chamber, configured to introduce a liquid;

a mechanical element configured to controllably and reversibly adjust the process volume, wherein pressure contained within the process chamber is rapidly adjustable.

In some embodiments of the pumping system, the mechanical element is a hydraulic piston.

In some embodiments of the pumping system, the mechanical element is configured both to controllably and reversibly mechanically seal the process chamber from the environment and controllably and reversibly reduce the process volume.

In some embodiments of the pumping system, the mechanical element is configured to controllably release the liquid out of the process chamber.

The pumping system may include multiple process chambers each with a distinct process volume, and wherein for each process chamber, there is a mechanical element configured to controllably and reversibly adjust the respective process volume of that process chamber.

DETAILED DESCRIPTION OF EMBODIMENTS OF THE INVENTION

Figure 1:
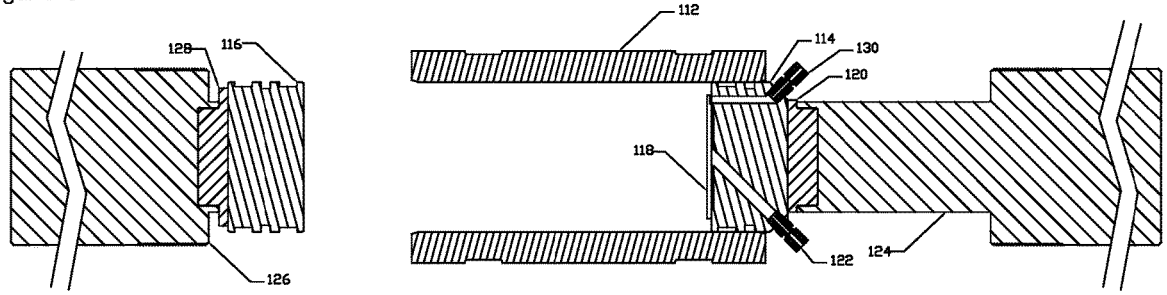
FIG. 1 depicts an exemplary embodiment of the invention with two moveable hydraulic pistons and a fixed process chamber, with the hydraulic pistons shown in the loading position.

The methods, systems, structures, and compositions of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in Markush groups. Thus in some embodiments not otherwise explicitly recited, any instance of "comprising" may be replaced by "consisting of" or, alternatively, by "consisting essentially of."

The present invention, in some variations, provides processes and apparatus using supercritical carbon dioxide as a solvent, in conjunction with low-temperature mechanical processing in an integrated unit. The disclosed processes and apparatus benefit from improved loading and unloading capabilities over currently available equipment and processes. The principles of the invention enable systems and methods that overcome the low throughput and low recovery rates associated with the prior art.

The present invention is suitable for recovering one or more products from a starting biomass material. A wide variety of biomass materials may be processed, including but not limited to botanical feedstocks. Botanical feedstocks may include whole plants, plant herbs, plant roots, plant flowers, plant fruits, plant leaves, plant seeds, plant beans, and combinations thereof. The biomass material may itself be a botanical product (available on the market) that may be further processed to recover a higher-value product. Other types of biomass materials that may be processed according to this disclosure include starchy biomass (e.g., corn or wheat); lignocellulosic biomass including agricultural residues (e.g., corn stover or wheat straw), hardwoods, or softwoods; energy crops; or municipal solid waste, for example.

The products that may be extracted from a starting biomass material also vary widely, depending on the selection of biomass. As just one example, a cannabidiol product may be extracted from hemp. As another example, essential oils may be extracted from citrus peels. As another example, lignin may be extracted from pretreated lignocellulosic biomass. Process operating parameters including extraction pressure, extraction temperature, extraction time, and extraction solvent may be adjusted to maximize the process efficiency and to target specific desired compounds.

Some variations of the invention provide a system configured for extracting one or more products from a biomass material, the system comprising:

a process chamber having an internal volume suitable for containing a biomass material and optionally an extraction solvent;

one or more mechanical elements configured to (i) controllably and reversibly mechanically seal the process chamber from the environment and (ii) controllably and reversibly reduce the internal volume to mechanically compress the biomass material within the process chamber;

a fluid port disposed in flow communication with the process chamber; and a collection sub-system disposed in flow communication with the fluid port, wherein the collection sub-system is configured to recover one or more products from the process chamber.

In some embodiments, at least one of the mechanical elements is a hydraulic piston. Preferably, a common mechanical element is configured both to controllably and reversibly mechanically seal the process chamber from the environment and controllably and reversibly reduce the internal volume to mechanically compress the biomass material within the process chamber. The process chamber may be a single-piston pressure chamber or a dual-piston pressure chamber, for example.

In some embodiments, at least one of the mechanical elements is configured to controllably compress the extraction solvent within the process chamber. In these or other embodiments, at least one of the mechanical elements is configured to controllably release the extraction solvent out of the process chamber through the fluid port.

Alternative mechanical elements include, but are not limited to, single screws, twin screws, rotors, gears, rams, and reciprocating chamber walls.

The extraction solvent may be selected from the group consisting of carbon dioxide, alkanes, alkenes, alcohols, water, and combinations thereof, for example.

In some embodiments, the collection sub-system includes at least one collection chamber having a collection volume, wherein the collection sub-system includes an additional mechanical element configured to controllably and reversibly adjust the collection volume. Because the collection volume is adjustable, and when there is a good seal, the collection pressure contained within the collection chamber is adjustable to assist in recovery of one or more products.

Some variations of the invention provide a system configured for extracting one or more products from a biomass material, the system comprising:

a process chamber having an internal volume suitable for containing a biomass material;

one or more mechanical elements configured to controllably and reversibly reduce the internal volume to mechanically compress the biomass material within the process chamber; and a collection sub-system disposed in flow communication with the process chamber, wherein the collection sub-system is configured to recover one or more products from the process chamber.

Some variations of the invention provide a system configured for extracting one or more products from a biomass material, the system comprising:

a process chamber having an internal volume suitable for containing a biomass material and optionally an extraction solvent;

one or more mechanical elements configured to controllably and reversibly reduce the internal volume to increase the pressure of the extraction solvent within the process chamber;

a fluid port disposed in flow communication with the process chamber; and a collection sub-system disposed in flow communication with the process chamber, wherein the collection sub-system is configured to recover one or more products from the process chamber.

Other variations of the present invention provide a method of extracting one or more products from a biomass material, the method comprising:

(a) introducing a starting biomass material into a process chamber;

(b) mechanically sealing the process chamber;

(c) mechanically compressing the starting biomass material to physically release at least a first fluid material, thereby generating a compressed biomass material;

(d) mechanically decompressing the compressed biomass material, thereby generating an intermediate biomass material;

(e) introducing an extraction solvent into the process chamber;

(f) maintaining process-chamber pressure from about 1 bar to about 1000 bar for an extraction time, wherein the extraction solvent extracts at least a second fluid material from the intermediate biomass material, thereby generating a left-over biomass material; and (g) recovering at least the second fluid material from the process chamber.

The order of steps may be varied, as will be appreciated by a person of ordinary skill in the art. For example, step (c) may be performed prior to step (b); and step (e) may be performed prior to, during, or after step (a), step (b), step (c), or step (d).

In some embodiments, the extraction solvent is pre-blended with the starting biomass material prior to step (b). Alternatively, or additionally, the extraction solvent may be introduced into the process chamber during step (b), step (c), and/or step (d), or between any of these steps, or after step (d).

In some embodiments, step (b) utilizes a hydraulic piston to mechanically seal the process chamber. The same hydraulic piston, or another hydraulic piston, may be utilized to mechanically compress the starting biomass material in step (c). Optionally, step (c) may be assisted by a solvent that dissolves or suspends the first fluid material; this solvent, when employed, may be the same or different than the extraction solvent. The hydraulic piston may be retracted prior to pumping extraction solvent into the process chamber, thereby increasing the volume of the process chamber while maintaining the seal so that the solvent is retained in the process chamber.

In step (f), the extraction solvent may be compressed using the same mechanical element as used in step (b), to reach the process-chamber pressure. In some embodiments, for example, a hydraulic piston is positioned to compress the extraction solvent to reach the process-chamber pressure.

In various embodiments, the extraction solvent is selected from the group consisting of carbon dioxide, alkanes (e.g., propane, isobutane, or n-hexane), alkenes (e.g., ethylene or cyclohexene), alcohols (e.g., ethanol or isobutanol), water, and combinations thereof. In some embodiments, the extraction solvent is liquid carbon dioxide, supercritical carbon dioxide, or a combination thereof. In some preferred embodiments, the extraction solvent is supercritical carbon dioxide.

The extraction solvent may be selected from the group consisting of carbon dioxide ($CO_2$), $C_1$-$C_4$ hydrocarbons (e.g., methane, ethane, ethylene, propane, propylene, or n-butane), $C_1$-$C_4$ oxygenates (e.g., methanol, ethanol, or acetone), and combinations thereof. For purposes of this disclosure, derivatives of hydrocarbons or oxygenates, in which one or more hydrogen atoms are replaced by other elements or functional groups, are included.

In some embodiments, the extraction solvent includes or consists essentially of carbon dioxide. The carbon dioxide may be in a supercritical state within the process chamber. Alternatively, or additionally, the carbon dioxide may be in a liquid state within the process chamber. The system optionally comprises a means for introducing solid carbon dioxide (also known as dry ice) into the process chamber.

Dilution gases may be included with the extraction solvent. For example, inert gases such as Ar or $N_2$ may be present along with $CO_2$, in an exemplary solvent.

Selection of temperature and pressure will generally depend on the desired product(s) and choice of extraction solvent.

In some embodiments, the process-chamber pressure (extraction pressure) is selected from about 50 bar to about 500 bar. In various embodiments, the extraction pressure is about, at least about, or at most about 1, 2, 3, 4, 5, 10, 15, 20, 25, 30, 40, 50, 60, 70, 80, 90, 100, 150, 200, 250, 300, 350, 400, 450, 500, 600, 700, 800, or 900 bar, for example.

The extraction time may be from about 0.1 minute to about 1 hour, for example. In various embodiments, the extraction time is about, at least about, or at most about 0.1, 0.2, 0.3, 0.4, 0.5, 1, 2, 3, 4, 5, 10, 15, 20, 25, 30, 40, 50, or 60 minutes, for example. The extraction time refers to the amount of time needed for the extraction to take place, once the extraction pressure and temperature are reached.

Step (f) may be carried out at an extraction temperature from about −50° C. to about 100° C., for example. In various embodiments, the extraction temperature is about, at least about, or at most about −40° C., −30° C., −20° C., −10° C., 0° C., 10° C., 20° C., 25° C., 30° C., 40° C., 50° C., 55° C., 60° C., 65° C., 70° C., 80° C., 90° C., or 95° C.

An extraction process may utilize a plurality of different pressures and/or temperatures, if desired, such as to target different compounds that have optimal extraction efficiencies at different conditions. For example, extraction may be conducted for a first period of time (e.g., 1 minute) at a first pressure (e.g., 100 bar) and a first temperature (e.g., 50° C.) followed by extraction at a second period of time (e.g., 2 minutes) at a second pressure (e.g., 200 bar) and a second temperature (e.g., 40° C.).

Certain embodiments utilize multiple process chambers that may each be operated at distinct extraction conditions. For example, a sequence of process chambers may be used in which the processed material from a first chamber, or a portion of the processed material (e.g., following a separation of solvent or biomass), becomes the feed material to a second process chamber.

In step (f), the ratio of the extraction solvent to the intermediate biomass material may be selected from about 1 to about 20 on a mass basis, for example. In various embodiments, the ratio of extraction solvent to the biomass material is about, at least about, or at most about 1, 2, 3, 4, 5, 6, 7, 8, 9, 10, 11, 12, 13, 14, 15, 16, 17, 18, 19, or 20, for example.

The process chamber may be agitated in a variety of ways. In some embodiments, the process chamber is disposed in physical communication with an external vibrating motor that physically vibrates the process chamber to mix the contents. In some embodiments, the process chamber is configured with a stirring mechanism such as an internal impeller or paddle. In some embodiments, the process chamber is agitated by rolling or tumbling the process chamber in an automated manner within the overall system.

In some embodiments, the process chamber is agitated via continuous recycling of extraction solvent that is pumped out of and back into the process chamber. In similar embodiments, continuous recirculation of an inert gas (such as Ar or $N_2$) through the process chamber may be employed to enhance the mixing efficiency. Combinations of any of these agitation techniques, or others (e.g., sonication), may be employed in certain embodiments.

Effective agitation ranges may vary and may be characterized by an output associated with the selected agitation means. For example, in the case of an external vibrating motor, the vibration frequency may be monitored or controlled. In the case of an internal impeller, the impeller revolution frequency (e.g., revolutions per minute, rpm) may be monitored or controlled. In the case of a continuous purge and reinjection of fluid or another gas, the recycle flow rate may be monitored or controlled, and so on.

For any type of agitation, the fluid Reynolds Number (Re) may be monitored, estimated, or controlled, such as by use of tracers to measure velocity distribution within the pressure vessel. The Re may be based on the process chamber diameter or on the impeller diameter in the case of an internal impeller, for example. In various embodiments, an effective internal Re may be from about 100 to about 10,000, for example. The flow pattern within the process chamber may be laminar or turbulent.

The specific agitation rate is not regarded as critical to the invention, and one skilled in the art will be able to employ an effective agitation rate. In some embodiments, a non-agitated process chamber (Re=0) is employed.

The system preferably includes a process chamber subsystem for adjusting temperature, pressure, and/or residence time within the process chamber. A reactor control subsystem may be configured to vary parameters during extraction, such as over a prescribed protocol, or in response to measured variables. For example, an unintended change in process chamber pressure may be compensated by a change in process chamber temperature and/or residence time. As another example, temperature may be maintained constant (isothermal operation) or pressure may be maintained constant (isobaric operation). The process chamber subsystem may utilize well-known control logic principles, such as feedback control and feedforward control. Control logic may incorporate results from previous experiments or production campaigns. One example of a process chamber subsystem is MasterLogic Programmable Logic Controller from Honeywell (Morris Plains, N.J., U.S.).

In some embodiments, the system further comprises a safety release line that is activated when the pressure within the process chamber reaches or exceeds a predetermined pressure, such as a pressure selected from 500 bar to 2000 bar that is higher than the desired extraction pressure within the process chamber.

Other safety considerations may be applied to the system and methods. The process chamber subsystem mentioned above may include protective devices that automatically shut down the operation, when the temperature or pressure exceeds a maximum value. Practical safety-related design may be built into the system as well. Those skilled in the art will understand how to design safe pressure vessels and systems employing them.

The method may further include recovering the first fluid material. The first fluid material and the second fluid material may be chemically the same or different.

In step (g), the second fluid material may be mechanically released from the process chamber. Typically, the extraction solvent is mechanically released along with the second fluid material, although the mechanical release may be sequential by varying pressure and/or temperature. In some embodiments, a hydraulic piston is used to mechanically release the second fluid material and the extraction solvent. In some embodiments, left-over biomass material is compressed by the hydraulic piston, which is convenient for recovery of the left-over biomass material.

Optionally, the method further comprises repeating steps (d), (e), and (f) a plurality of times. During cycling, the process-chamber pressure, the extraction time, and/or extraction temperature may be adjusted.

Other variations of the present invention provide a method of extracting one or more products from a biomass material, the method comprising:

(a) introducing a biomass material into a process chamber;

(b) mechanically sealing the process chamber;

(c) introducing an extraction solvent into the process chamber;

(d) mechanically compressing the extraction solvent to increase process-chamber pressure;

(e) maintaining process-chamber pressure from about 1 bar to about 1000 bar for an extraction time, wherein the extraction solvent extracts a fluid material from the biomass material, thereby generating a left-over biomass material; and (f) recovering the fluid material from the process chamber.

Some variations of the disclosure provide a collection system configured for recovering one or more products from an extracted biomass material, the collection system comprising:

at least one collection chamber having a collection volume;

an inlet to the collection chamber, configured to introduce a biomass-extraction liquid;

a mechanical element configured to controllably and reversibly adjust the collection volume, wherein collection pressure contained within the collection chamber is adjustable to assist in recovery of one or more products from the biomass-extraction liquid.

In some embodiments of the collection system, the mechanical element is a hydraulic piston.

In some embodiments of the collection system, the mechanical element is configured both to controllably and reversibly mechanically seal the collection chamber from the environment and controllably and reversibly reduce the chamber volume.

In some embodiments of the collection system, the mechanical element is configured to controllably release the biomass-extraction liquid out of the collection chamber.

The collection system may include multiple collection chambers each with a distinct collection volume, wherein for each collection chamber, there is a mechanical element configured to controllably and reversibly adjust the respective collection volume of that collection chamber.

Within a collection system, a collection chamber as described above may be optimized in temperature and/or pressure (and potentially other conditions such as time or pH). Such optimization of conditions enables a collection chamber to function as an evaporator, a dryer, a distillation stage (and multiple chambers as multiple distillation stages), a selective-precipitation unit, a filter, or another type of separation unit operation.

Still other variations of the disclosure provide a pumping system configured for pumping a liquid into a process chamber, the pumping system comprising:

at least one process chamber having a process volume;

an inlet to the process chamber, configured to introduce a liquid;

a mechanical element configured to controllably and reversibly adjust the process volume, wherein pressure contained within the process chamber is rapidly adjustable.

In some embodiments of the pumping system, the mechanical element is a hydraulic piston.

In some embodiments of the pumping system, the mechanical element is configured both to controllably and reversibly mechanically seal the process chamber from the environment and controllably and reversibly reduce the process volume.

In some embodiments of the pumping system, the mechanical element is configured to controllably release the liquid out of the process chamber.

The pumping system may be adapted to receive material from a conventional pump (e.g., a centrifugal pump, a positive-displacement pump, an axial-flow pump, etc.) at a relatively low pressure, such as about 1-10 bar. The use of the hydraulic piston or other mechanical element enables feeding into a process chamber that may be pressurized to much higher pressures (such as about 10-500 bar) arising from the volume reduction due to movement of hydraulic piston.

The pumping system may include multiple process chambers each with a distinct process volume, and wherein for each process chamber, there is a mechanical element configured to controllably and reversibly adjust the respective process volume of that process chamber.

Certain embodiments of the invention will now be described in more detail, without intending to limit the invention in any way.

Also, the following description is largely in reference to carbon dioxide as part or all of the extraction solvent. It will be understood that the present invention is by no means limited to carbon dioxide ($CO_2$). An operator may desire to introduce other solvents to target products not easily recoverable by liquid or supercritical $CO_2$, or to change the viscosity of the extracted products. Other solvents may be used alone or as cosolvents in combination with liquid or supercritical $CO_2$.

In some embodiments, the equipment and process are designed to greatly speed up the extraction step by combining the ability to mechanically extract at low temperature (e.g., under about 60° C.) by using a hydraulic piston with the ability to use supercritical carbon dioxide in a single process chamber. The hydraulic piston(s) control the volume of the process chamber and consequently the pressure (inverse correlation), thereby allowing the operating pressure to be reached very quickly as well as allowing the operating pressure to be quickly and easily adjusted.

In some embodiments, a pump is employed to introduce liquid carbon dioxide into a process chamber. Because the liquid carbon dioxide may be introduced prior to mechanical compression of the process chamber, the pump may be operated at a very high rate. In conventional approaches in which high-pressure carbon dioxide needs to be pumped into a reactor, the rate is severely limited due to enormous pumping energy (and thus pump size and cost) that is necessary to pump against the high pressure. In the present invention, by contrast, high rates of carbon dioxide (or other extraction solvent) may be introduced, followed by a pressure increase via the hydraulic piston. The flow of supercritical carbon dioxide out of the process chamber with dissolved and/or entrained extracted fluids is controlled by the hydraulic system and the extraction system and is not limited by the liquid carbon dioxide pump.

One of the challenges with conventional equipment is long loading, unloading, and cleaning times involved with removing processed material and reloading fresh material. This invention addresses this known problem by allowing the top (or, one end) of the process chamber to be easily and quickly accessed with a movable hydraulic piston. At the end of the cycle, the processed material may be compressed to a solid puck and pushed out (via hydraulic piston) of the bottom of the process chamber.

Generally, the disclosed systems and processes are designed to greatly speed up the extraction step. The improvement over current state-of-the-art equipment equates to approximately a ten-fold improvement in organic material throughput, allowing for a much better processing ability for large-scale producers. This process, in some embodiments, uses less than half as much carbon dioxide during the extraction process to remove the same amount of recoverable oils.

Additional throughput improvements may be realized by reducing loading, unloading, and cleaning times. A dual-piston process chamber makes loading very fast. The upper piston pushes a processed and compressed (densified) puck of organic material out of the process chamber at the end of the cycle. Optionally, carbon dioxide may be used within an empty vessel to clean the inside of the process chamber and the extraction tubes when desired.

The disclosed design offers greater flexibility in operation compared to current commercially available machines. For example, in certain embodiments, dry ice (frozen $CO_2$) may be simply added directly into the process chamber along with the biomass material. If other solvents are utilized, they can also be used and expelled at the end of the cycle using hydraulic pistons to carry the solvents out of the process chamber.

In some embodiments, a dual-piston chamber may be used in a cold-press mode. In these embodiments, the biomass material is added to the process chamber, optionally with a carrier oil to help capture the desired essential oils from the botanicals. The carrier oil and captured essential oils are squeezed out of the botanicals by direct pressure via mechanical forces. A sealed chamber is not necessary to develop internal pressure, in these embodiments.

In some variations of the invention, an extraction process is predicated on the use of a process chamber with an internal volume that is adjustable by means of a mechanical element, such as (but not limited to) a hydraulic piston. The adjustable volume enables one to swiftly and easily adjust the pressure inside the process chamber, and to speed up loading and extraction of the biomass. For example, using one or more hydraulic pistons to seal and pressurize the process chamber allows for extracting biomass material with a cold-press method, a solvent extraction method, or both in combination to achieve excellent recovery rates and throughput speeds.

Some embodiments provide a system employing two moveable hydraulic pistons attached to heads that extend into a fixed process chamber. The system is typically arranged vertically so that there is an upper piston and a lower piston. The upper piston is used for loading and controlling process-chamber pressure. The lower piston is used for unloading and is fixed during processing. There is at least one port on one of the piston heads (generally the lower piston head) to allow fluids pressed out to escape, and to allow solvent to flow in and out.

Some embodiments provide a system with one moveable hydraulic piston attached to a head that extends into a moveable process chamber. This system is typically arranged vertically, with the motion of the process chamber limited to the axis of the hydraulic piston. The lower piston head is fixed and the process chamber moves off of it at the end of the cycle to allow for unloading.

It is noted that by use of a hydraulic piston or other functionally equivalent mechanical element, the physical pressure that may be exerted on the material can be very high, such as up to 5000 bar or higher, by simply changing the chamber diameter and shape of piston head. The minimum and maximum volume of a given process chamber may be varied in the initial design. During operation, adjustment of volume (via hydraulic piston movement) allows easy adjustment and optimization of process pressure.

Some embodiments provide a collection system connected to the process chamber to collect the supercritical carbon dioxide and separate that solvent from the desired extracted products. A number of collection chambers at different pressures allows for separation of products based on density and/or solvency in the supercritical carbon dioxide at different pressures, for example. Some products may need only a single collection chamber, while some extracts contain a wide range of different compounds and it may be desirable to separate them during the collection process to simplify processing after this system. Some collection chambers may require, or benefit from, added heat in order to control the temperature throughout. In some embodiments employing supercritical carbon dioxide, the solvent changes state from a liquid to a gas and experiences a large pressure drop across the collection system.

Some embodiments utilize an automated system to feed material into the process chamber and to collect the raffinate at the end of the cycle, to increase throughput and to reduce the cost of running the system.

The system may be a batch apparatus, a continuous apparatus, a semi-continuous apparatus, or a combination thereof. The designs disclosed herein can be adapted using known chemical-engineering principles to any scale system for production of large, commercial volumes of products.

The selection of the materials of construction for the system will be dependent on the desired properties and should be considered on a case-by-case basis. Someone skilled in the art of material science or metallurgy will be able to select the appropriate materials for the intended use, based on the information provided in this disclosure.

Some embodiments of the invention will now be described with reference to the accompanying drawings (FIGS. 1 to 11), which are non-limiting.

As depicted in FIG. 1, a system designed to operate up to 500 bar is characterized by a process chamber 112 composed of stainless steel or other material capable of withstanding the operating pressures and that is safe to expose to biomass and the solvents used in the process. The process chamber 112 is rigidly held, and two moveable hydraulic pistons 124 and 126 connected to pressure plates 114 and 116 via attachment means 120 and 128, respectively, can move independently to control the pressure inside the process chamber 112, for loading biomass at the beginning of the cycle, adjusting the pressure during processing, expelling the solvent and dissolved or entrained chemicals, and expelling the processed material at the end of the cycle. At least one of the pressure plates 114 or 116 has at least one orifice 122 through which liquid or supercritical $CO_2$ and/or other fluids can be introduced into the sealed chamber and through which pressed fluids can be removed from the process chamber 112. At the end of the processing cycle, the solvent and dissolved chemicals may be expelled through the orifice 122. The solvent and dissolved or entrained chemicals may be separated in a collection system (not shown in FIG. 1).

A typical process begins with one pressure plate 114, held inside the process chamber, creating a cylinder with one open end. A known amount of biomass material is introduced to this chamber volume. The mass of biomass placed in the chamber volume may be predetermined based on the oil content of the biomass, the type of solvent used, and the number of extraction cycles.

After a predetermined amount of biomass is added to the process chamber, pressure plate 116 is extended into the process chamber 112 to seal the pressure. Port 122 is opened and the pressure plate 116 is further extended to apply pressure to the biomass material. Oil and fluids are pressed out and collected through port 122. In some embodiments, after the cold press, orifice 122 is sealed shut and liquid $CO_2$ is pumped into the process chamber 112 through orifice 122 by a connected carbon dioxide pump (not shown in FIG. 1). The process chamber 112 can be heated or cooled to provide a stable and consistent operating temperature. Pressure plate 116 can be moved to keep the pressure low inside the process chamber 112 until the desired mass of liquid $CO_2$ has been introduced. Orifice 122 is closed again and pressure plates 114 and 116 can be moved individually or in concert to increase the pressure inside the process chamber 112 to the desired operating pressure and optionally to change the $CO_2$ from a liquid to a supercritical fluid. This pressure increase typically takes only a few seconds.

Following extraction, when the supercritical $CO_2$ is saturated or has dissolved all the desired oils, orifice 122 is opened. Valving directs the outflow to a collection system, where the liquid or supercritical carbon dioxide may be converted to a gas separated from the extracted oils. Pressure plates 114 and 116 can be moved individually or in concert to adjust the flow rate out of the process chamber 112, and to squeeze the biomass material into a dense puck. Pressure plate 116 has a removable screen 118 that allows the solvents, dissolved oils, and air or other gases to pass freely across the screen 118 while stopping the biomass material from exiting the process chamber 112 and entering orifice 122 or collection system. The valving is adjusted to allow the interior of process chamber 112 to equalize to ambient pressure. Pressure plate 114 is withdrawn from process chamber 112 and pressure plate 116 is extended to push out the raffinate material. The pressure plates can be repositioned to their first positions and the process repeated, as desired.

Figure 2:
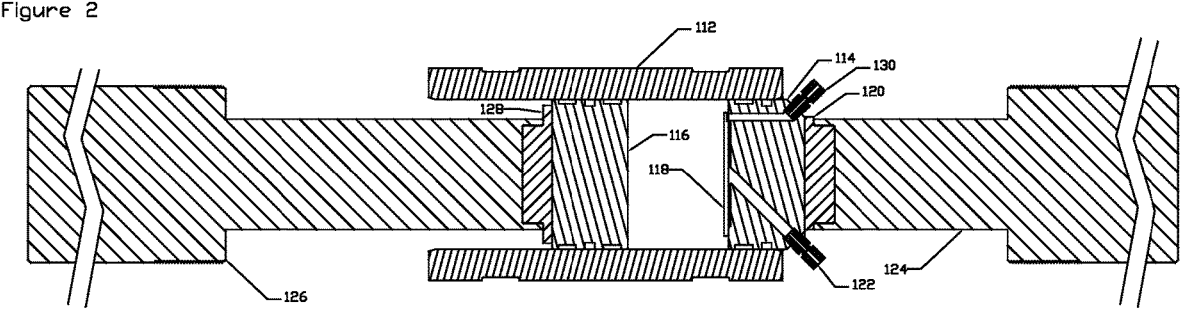
FIG. 2 depicts an exemplary embodiment of the invention with two moveable hydraulic pistons and a fixed process chamber, with the hydraulic pistons shown in the processing position.
Figure 3:
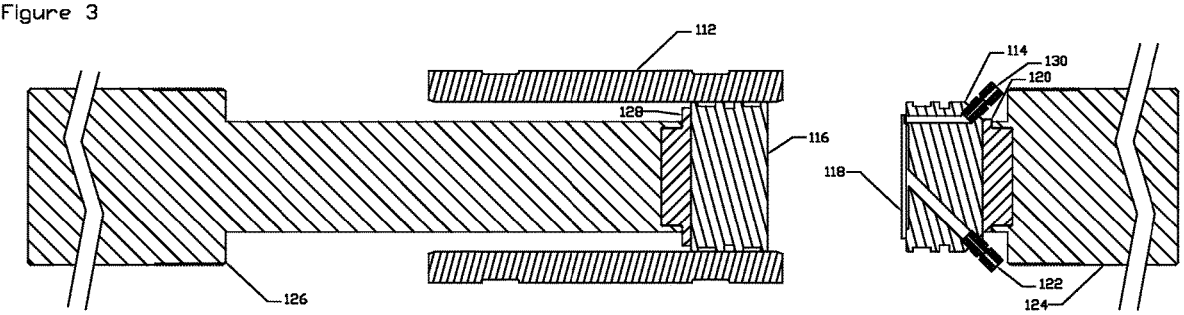
FIG. 3 depicts an exemplary embodiment of the invention with two moveable hydraulic pistons and a fixed process chamber, with the hydraulic pistons shown in the unloading position.

FIG. 1 through FIG. 3 depict a process chamber arranged with two moveable pistons 124 and 126 with a fixed process chamber 112 and demonstrate how the pistons move during loading, processing, and unloading steps.

FIG. 1 depicts the fixed chamber 112 with two moveable hydraulic pistons 124 and 126 attached to the heads 116 and 114 that are used to seal and control the pressure in the process chamber 112. The hydraulic pistons are shown in the loading position, with one end of the process chamber open and the other sealed. Material is loaded into the open end of the process chamber.

FIG. 2 depicts the position of the moveable pistons in the processing step. Material inside the process chamber is compressed by the pistons 126 and 124. If port 122 is open, fluids pressed out of the process material are directly expelled. Solvents or process fluids can be introduced through input port 130. If port 122 is closed, the interior pressure of the process chamber is controlled by the position of the hydraulic pistons, allowing a solvent to interact with the process material at a controlled pressure. When exit port 122 is opened, the solvent and extracted fluids are directly expelled. The head 114 has a filter plate 118 covering the input and output ports to keep unwanted material out of the ports 122 and 130.

FIG. 3 depicts the position of the moveable pistons in the unloading step. Piston 124 is withdrawn from the process chamber 112 and the opposing piston 126 is extended, pushing any material present in the process chamber out and clearing the process chamber.

FIGS. 4 to 7 depict another method of arranging the moveable piston and process chamber. This arrangement has one moveable piston 426, one fixed head 414 attached to a fixed block 424, and a moveable process chamber 412. These figures demonstrate the open, loading, processing, and unloading steps.

Figure 4:
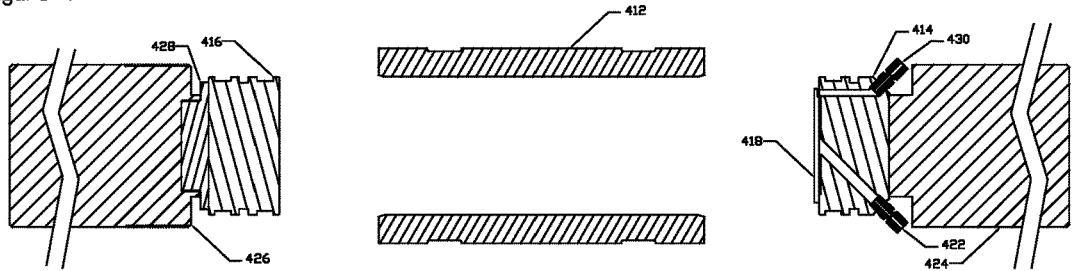
FIG. 4 depicts an exemplary embodiment of the invention with one moveable hydraulic piston, one fixed head attached to a fixed block, and a moveable process chamber, with the components in the open position.

FIG. 4 depicts the components in the open position.

Figure 5:
FIG. 5 depicts an exemplary embodiment of the invention with one moveable hydraulic piston, one fixed head attached to a fixed block, and a moveable process chamber, with the components in the loading position.

FIG. 5 depicts the components in the loading position. The moveable process chamber 412 is positioned over the fixed head 414 to seal one end of the process chamber. Process material is loaded into the open end of the process chamber.

Figure 6:
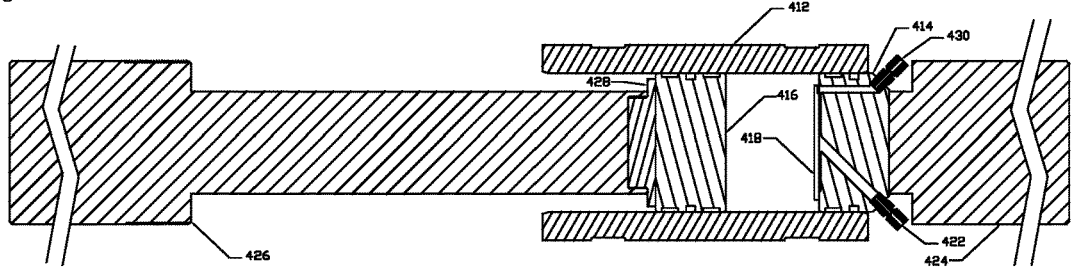
FIG. 6 depicts an exemplary embodiment of the invention with one moveable hydraulic piston, one fixed head attached to a fixed block, and a moveable process chamber, with the components in the processing position.

FIG. 6 depicts the position of the components in the processing step. Material inside the process chamber is compressed between the sealing head 416 attached to the moveable piston 426 and fixed head 414. If port 422 is open, fluids pressed out of the process material are directly expelled. Solvents or process fluids can be introduced through input port 430. If port 422 is closed, the interior pressure of the process chamber is controlled by the position of the hydraulic pistons, allowing a solvent to interact with the process material at a controlled pressure. When exit port 422 is opened, the solvent and extracted fluids are directly expelled. The head 414 has a filter plate 418 covering the input and output ports to keep unwanted material out of the ports 422 and 430.

Figure 7:
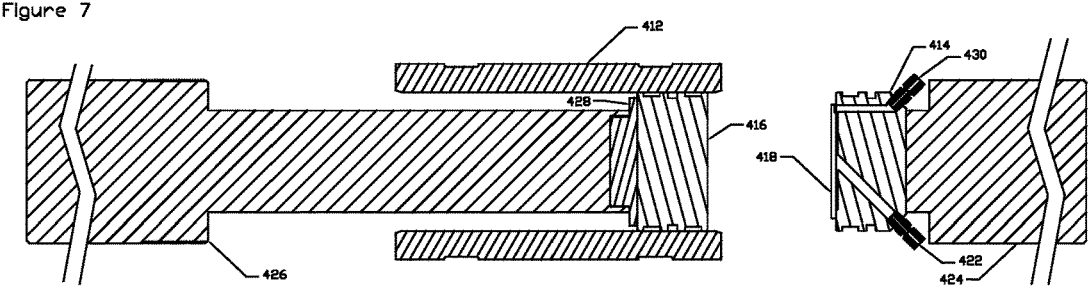
FIG. 7 depicts an exemplary embodiment of the invention with one moveable hydraulic piston, one fixed head attached to a fixed block, and a moveable process chamber, with the components in the unloading position.

FIG. 7 depicts the position of the components in the unloading step. Moveable process chamber 412 is withdrawn from the fixed sealing head 414 and moveable piston 426 is held stationary, pushing any material present in the process chamber out and clearing the process chamber.

Figure 8:
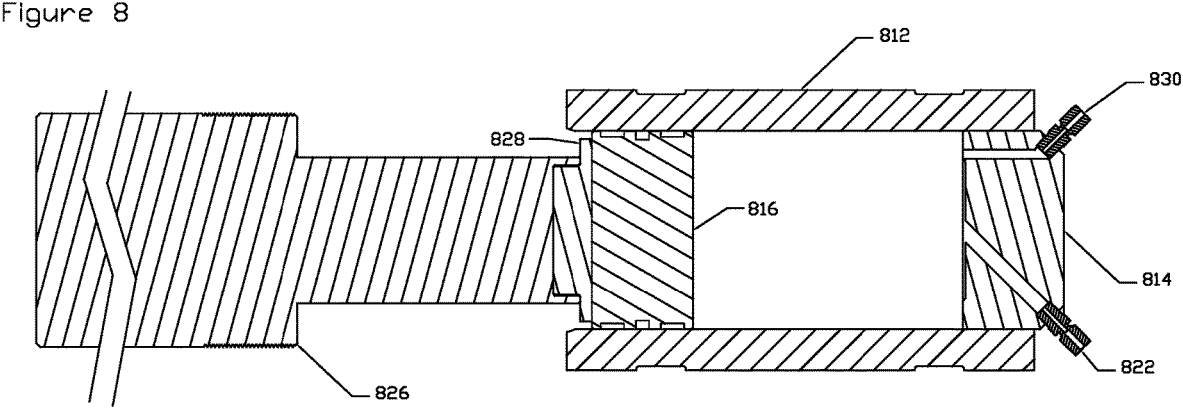
FIG. 8 depicts an exemplary embodiment of the invention with a secondary pressure chamber which can be used to store process fluids, as well as to control the pressure of those fluids, showing the secondary pressure chamber in the full position.
Figure 9:
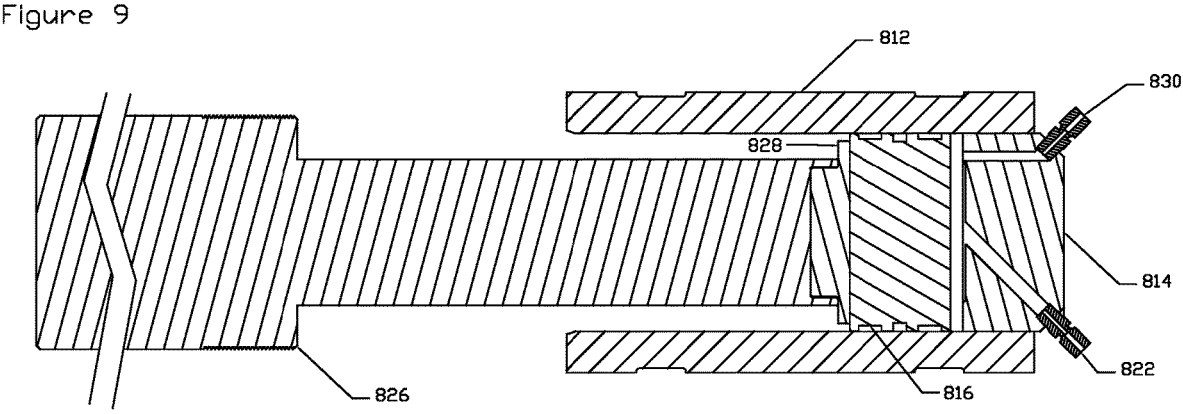
FIG. 9 depicts an exemplary embodiment of the invention with a secondary pressure chamber which can be used to store process fluids, as well as to control the pressure of those fluids, showing the secondary pressure chamber in the extended position.

FIG. 8 and FIG. 9 depict a secondary pressure chamber 812 which can be used to store process fluids, as well as to control the pressure of those fluids.

FIG. 8 depicts the secondary pressure chamber 812 in the full position. The process fluids can be prepared and moved into the secondary pressure chamber 812 under low pressure through input port 830. Moveable piston 826 can be positioned to control the interior pressure, allowing for the fluid to be introduced at a high flow rate. Moveable piston 826 can be extended or retracted to control the pressure inside the pressure chamber 812.

FIG. 9 depicts the moveable piston 826 in the extended position. This moves a fixed volume of fluid out of the pressure chamber 812 through exit port 822. The process fluid can be introduced into the previously described process chambers.

Figure 10:
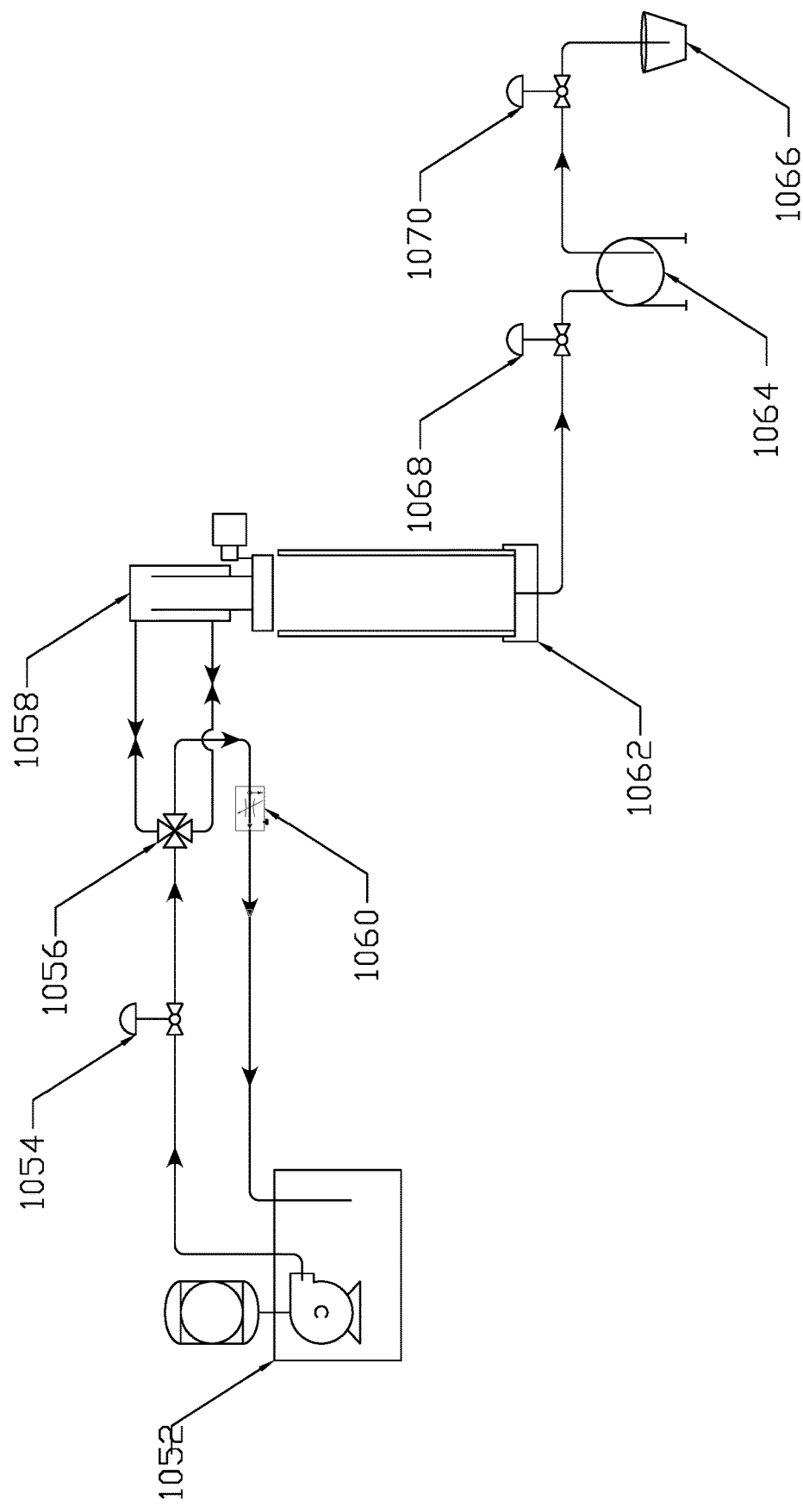
FIG. 10 depicts an exemplary embodiment of the invention with a process chamber with moveable hydraulic piston and a collection system attached to the process chamber.

FIG. 10 depicts the process chamber 1062 with moveable hydraulic piston 1058 and its pump 1052 and control hardware. A collection system is attached to the process chamber 1062. This collection system is used to capture the extracted fluids to separate a solvent that is a gas at ambient pressure and temperature. The extracted fluids are collected at a controlled pressure into collection chamber 1064. The solvent is separated as it becomes a gas and the extracted fluids remain in the liquid state. The gaseous solvent and residual pressure are relieved through control valve 1070 and residual collection vessel 1066 collects any remaining fluids carried by the flow of solvent.

Figure 11:
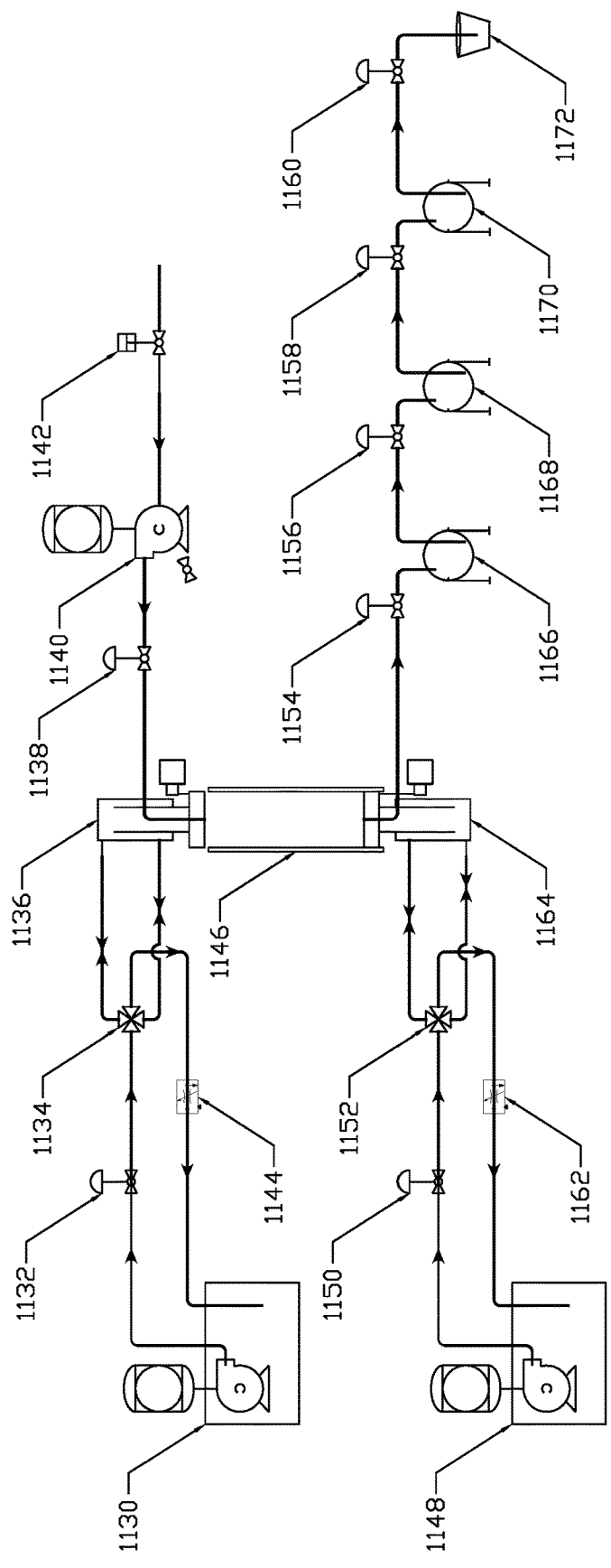
FIG. 11 depicts an exemplary embodiment of the invention with a process chamber with upper moveable hydraulic piston, a second lower moveable hydraulic piston, and a collection system with a number of collection chambers.

FIG. 11 depicts the process chamber with upper moveable hydraulic piston 1136 along with its pump 1130 and control hardware. A second lower moveable hydraulic piston 1164 and its pump 1148 and control hardware is also shown. Pump 1140 can move solvents or other fluids into the process chamber 1146. A collection system with a number of collection chambers 1166, 1168, 1170, and 1172 at different pressures is shown. Each collection chamber is at a controlled pressure as the extracted fluids flow through the collection system. Different compounds are released at each collection chamber.

Example 1: Supercritical $CO_2$ Extraction Process

An exemplary process starts with dried and shredded or whole botanical material loaded into a process chamber. An upper piston is withdrawn and the top of the process chamber is open to allow ease of access to automated loading systems.

A preset amount of biomass is loaded into process chamber. The amount of material per load is generally determined by the amount of extractable fluid versus the volume of $CO_2$ in the chamber. Typical ratios range from 2:1 to 20:1 by mass $CO_2$:organics.

The process chamber is sealed by extending the hydraulic piston.

Air is expelled by compression using the hydraulic piston. This step is optional.

The hydraulic piston is retracted and liquid carbon dioxide at about 83 bar is pumped through a port into the process chamber.

The fluid is compressed using the hydraulic piston to increase the pressure to the desired range of about 100-275 bar.

A valve is opened to allow the supercritical $CO_2$ to flow to the collection system, carrying the dissolved fluids. The hydraulic piston is extended to push all of the liquid or supercritical carbon dioxide out of the chamber. This step can also compress the left-over botanical material into a convenient solid puck.

Optionally, clean $CO_2$ is pumped into the process chamber, and the above steps are repeated to recover more oils or to target the extraction of different oils at different pressures and/or temperatures.

Optionally, oil lines are cleaned by running clean supercritical carbon dioxide fluid through the system to clean the vessel and tubes.

The upper hydraulic piston is retracted and the process chamber is prepared for the next load.

Example 2: Cold Press Process

An exemplary process starts with dried and shredded or whole botanical material loaded into a process chamber. An upper piston is withdrawn and the top of the process chamber is open to allow ease of access to automated loading systems.

A preset amount of biomass is loaded into the process chamber.

The biomass is compressed using a hydraulic piston, releasing oil from the biomass.

Oil is collected at an outlet at the bottom of a collection chamber.

The densified biomass is ejected.

The upper hydraulic piston is retracted and the process chamber is prepared for the next load.

Example 3: Combined Cold Press and Supercritical Carbon Dioxide Process

An exemplary process starts with dried and shredded or whole botanical material loaded into a process chamber. An upper piston is withdrawn and the top of the process chamber is open to allow ease of access to automated loading systems.

A preset amount of biomass is loaded into the process chamber. The amount of material per load is generally determined by the amount of extractable fluid left in the material after the cold press step (below) versus the volume of $CO_2$ in the chamber. Typical ratios range from 2:1 to 20:1 by mass $CO_2$:organics.

The process chamber is mechanically sealed by extending a hydraulic piston.

The biomass material is compressed with the hydraulic piston.

Oil is collected at an outlet at the bottom of a collection chamber. The valve to this outlet is closed.

The hydraulic piston is retracted and liquid carbon dioxide is pumped into the process chamber, at a pressure of about 83 bar.

The fluid is compressed using the hydraulic piston to increase the pressure to the desired range of about 100-275 bar.

The valve is opened to allow supercritical $CO_2$ to flow to the collection system, carrying the dissolved fluids. The hydraulic piston is extended to push all of the liquid or supercritical carbon dioxide out of the process chamber. This step can also compress the left-over botanical material into an easy-to-convey solid puck.

Optionally, clean $CO_2$ is pumped into the process chamber, and the above steps are repeated to recover more oils or to target the extraction of different oils at different pressures and/or temperatures.

Optionally, oil lines are cleaned by running clean supercritical carbon dioxide fluid through the system to clean the vessel and tubes.

The upper hydraulic piston is retracted and the process chamber is prepared for the next load.

Example 4: Oil Extraction from Hemp

In this example, the biomass material is hemp flowers dried to less than 15 wt % moisture content and containing 5 wt % to 25 wt % CBD and other desirable oils. The dried flowers are shredded to reduce particle size. The solvent used to extract CBD and other desirable oils is supercritical $CO_2$. The mass of hemp processed is determined by the ratio of recoverable oils present in the hemp and the mass of $CO_2$ that must be added to strip those oils out. The mass proportion of hemp within the processing chamber to the mass of $CO_2$ is typically in the range of 1:2 to 1:20. This ratio can be adjusted by performing multiple supercritical $CO_2$ extraction steps on the same biomass material.

Current processing equipment has the capability to only process approximately 0.1 pound of dried hemp per minute to extract cannabidiol (CBD) and other oils. Conventionally, the amount of $CO_2$ used is often in excess of 50 pounds $CO_2$ per pound of hemp during a continuous flow operation. Since so much carbon dioxide is used versus the amount of hemp processed, one of the major limiting factors in the throughput of conventional processes is the $CO_2$ pump's ability to flow carbon dioxide through a process chamber at the desired pressure. The carbon dioxide must be pressurized (to greater than 74 bar and heated to above 31° C.) in order to reach the supercritical state. Typical operating pressures for extracting CBD oils are 83 bar to 276 bar.

By contrast, the liquid carbon dioxide pump is used to initially fill the process chamber, but the carbon dioxide pump is not utilized to produce the pressure needed to bring the process chamber to its operating pressure. Instead, the hydraulic piston moves to decrease the chamber volume, thereby increasing the carbon dioxide pressure (according to the $CO_2$ thermodynamic equation of state) and allowing operating pressure to be reached very quickly, since mass transfer is rapid and equilibrium is attained quickly. This system also allows the supercritical carbon dioxide containing the dissolved oils and cannabinoids to be extracted very quickly and sent to the collection system.

Example 5: Oil Extraction from Hemp

In this example, the biomass material is hemp flowers dried to 12 wt % moisture content and containing 15 wt % CBD and other desirable oils. The dried flowers are shredded to reduce particle size. The solvent used to extract CBD and other desirable oils is supercritical $CO_2$. The mass of hemp processed is determined to be 100 grams so that mass ratio of hemp to $CO_2$ is 1:15 in the process chamber. This ratio allows for the most efficient use of the carbon dioxide. After the hemp flower is loaded, the system is sealed and liquid $CO_2$ is introduced. The liquid $CO_2$ pump is used to increase the pressure inside the process chamber to approximately 140 bar. The hydraulic piston is used to increase the pressure to 310 bar for 15 seconds.

The outlet valve to the collection system is opened, and pressure at the collection chambers is maintained at 82 bar and 40 bar, respectively. The hydraulic piston expels the $CO_2$ and compresses the processed hemp material into a solid puck. During this process, oils comprising 33% cannabidiolic acid (CBDA) are collected at a yield of 10 grams of oil per 100 grams of hemp.

In this detailed description, reference has been made to multiple embodiments and to the accompanying drawings in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A method of extracting one or more products from a biomass material, said method comprising:
    (a) introducing a starting biomass material into a process chamber having an internal volume that is adjustable by means of a hydraulic piston, wherein step (a) comprises (i) opening said process chamber by retracting said hydraulic piston, thereby creating a chamber open end, and (ii) directly loading said starting biomass material through said chamber open end and into said process chamber;
    (b) after loading a predetermined amount of said starting biomass material into said process chamber, extending said hydraulic piston toward said process chamber, thereby mechanically sealing said process chamber;
    (c) mechanically compressing said starting biomass material to physically release at least a first fluid material, thereby generating a compressed biomass material;
    (d) mechanically decompressing said compressed biomass material, thereby generating an intermediate biomass material;
    (e) introducing an extraction solvent into said process chamber;
    (f) maintaining process-chamber pressure from about 1 bar to about 1000 bar for an extraction time, wherein said process-chamber pressure is controlled by said hydraulic piston, and wherein said extraction solvent extracts at least a second fluid material from said intermediate biomass material, thereby generating a left-over biomass material; and
    (g) recovering at least said second fluid material from said process chamber.

2. The method of claim 1, wherein said extraction solvent is pre-blended with said starting biomass material prior to step (b).

3. The method of claim 1, wherein said extraction solvent is introduced into said process chamber during step (b), step (c), and/or step (d).

4. The method of claim 1, wherein step (c) utilizes said hydraulic piston to mechanically compress said starting biomass material.

5. The method of claim 1, wherein in step (f), said hydraulic piston is positioned to compress said extraction solvent to reach said process-chamber pressure.

6. The method of claim 1, wherein in step (f), said extraction solvent is compressed using said hydraulic piston, to reach said process-chamber pressure.

7. The method of claim 1, wherein in step (f), said extraction solvent is compressed using a common mechanical element as used in step (c), to reach said process-chamber pressure.

8. The method of claim 1, wherein said process-chamber pressure is selected from about 50 bar to about 500 bar.

9. The method of claim 1, wherein said extraction solvent is selected from the group consisting of carbon dioxide, alkanes, alkenes, alcohols, water, and combinations thereof.

10. The method of claim 1, wherein said extraction solvent is liquid carbon dioxide, supercritical carbon dioxide, or a combination thereof.

11. The method of claim 10, wherein said extraction solvent is supercritical carbon dioxide.

12. The method of claim 1, wherein said extraction time is from about 0.1 minute to about 1 hour.

13. The method of claim 1, wherein step (f) is carried out at an extraction temperature from about −50° C. to about 100° C.

14. The method of claim 1, wherein in step (f), the ratio of said extraction solvent to said intermediate biomass material is selected from about 1 to 20 on a mass basis.

15. The method of claim 1, said method further comprising recovering said first fluid material, wherein optionally said first fluid material and said second fluid material are chemically the same.

16. The method of claim 1, wherein in step (g), said second fluid material is mechanically released from said process chamber.

17. The method of claim 16, wherein said hydraulic piston is used to mechanically release said second fluid material and said extraction solvent.

18. The method of claim 17, wherein said left-over biomass material is compressed by said hydraulic piston, and wherein said left-over biomass material is recovered.

19. The method of claim 1, said method further comprising repeating steps (d), (e), and (f) a plurality of times, wherein optionally said process-chamber pressure, said extraction time, and/or extraction temperature are adjusted.

* * * * *